United States Patent [19]

Porteous

[11] Patent Number: 5,004,418
[45] Date of Patent: Apr. 2, 1991

[54] DENTAL INSTRUMENT MAT

[76] Inventor: Paul D. Porteous, 607 Island View Dr., Port Hueneme, Calif. 93041

[21] Appl. No.: 460,524

[22] Filed: Jan. 3, 1990

[51] Int. Cl.$^5$ .............................................. A61G 15/00
[52] U.S. Cl. ...................................... 433/77; 206/369
[58] Field of Search ................. 433/77; 206/368, 369, 206/564, 565; 248/117.2, 117.6, 682

[56] References Cited

U.S. PATENT DOCUMENTS

| | | | |
|---|---|---|---|
| 3,285,409 | 11/1966 | Loran | 206/564 X |
| 3,532,221 | 10/1970 | Kaluhiokalani et al. | 206/564 X |
| 3,589,511 | 6/1971 | Britt | 206/564 X |
| 3,634,937 | 1/1972 | Green | 433/77 X |
| 3,982,630 | 9/1976 | Garnier | 206/369 |
| 4,572,371 | 2/1986 | Asenbauer | 206/564 X |
| 4,852,738 | 8/1989 | Craig et al. | 206/369 |

*Primary Examiner*—Robert P. Swiatek
*Assistant Examiner*—Nicholas D. Lucchesi
*Attorney, Agent, or Firm*—Donald Diamond

[57] ABSTRACT

A dental instrument mat includes a base portion having two opposite sides and two opposite ends and a pair of racks formed longitudinally along the two opposite sides. Each rack has a plurality of spaced apart teeth, and the teeth of each rack are laterally aligned with teeth of the other rack to form a plurality of laterally disposed holding slots. An elastic band is looped over protrusions formed at the opposite axial ends of the base portion so as to place the elastic band in tension and thereby hold dental instruments in the holding slots during autoclaving.

9 Claims, 2 Drawing Sheets

DENTAL INSTRUMENT MAT

BACKGROUND OF THE INVENTION

1. Field of the Invention

The present invention relates generally to holding and organizing devices and, more specifically to a dental instrument mat which can be placed in an autoclave for sterilizing dental instruments.

2. Description of the Related Art

Dental instrument mats are generally known and widely used by dentists to organize a variety of dental instruments while working a patient. Typically, the dental instrument mat includes a pair of longitudinally disposed racks, each having a plurality of spaced apart teeth which extend upwardly from a base portion. The teeth of the two racks are laterally aligned to form a plurality of laterally disposed holding slots, each being adapted to receive a dental instrument. When the dental instrument mat is placed on a tray, with the plurality of dental instruments resting in the plurality of holding slots, a dentist is able to keep his instruments organized while working on a patient.

After the dentist has finished a dental procedure, the instruments are cleaned and then placed longitudinally in a space between the two racks of the dental instrument mat, whereupon the mat is then placed in a sterilizing pouch which is then placed in an autoclave for sterilization. After sterilization, the mat and instruments are removed from the autoclave and the pouch and then the instruments are rearranged in the holding slots according to a desired order, which may be dictated by the dental procedure to be performed by the dentist.

In the sterilization process, the instruments must be handled when placing them in the space between the two racks and, following sterilization, when placing them back in the holding slots. Thus, after sterilization, the instruments must be handled prior to use by the dentist, thereby presenting a problem of potential contamination. Moreover, the additional handling steps require time and labor.

SUMMARY OF THE INVENTION

An object of the present invention is to provide a dental instrument mat with retaining means for holding dental instruments in their corresponding holding slots prior to, during and after autoclaving. Another object of the present invention is to provide a dental instrument mat which is relatively simple in construction and cost effective to produce.

Another object of the present invention is to reduce the number of steps required to perform a sterilization procedure for sterilizing dental instruments.

These and other objects of the present invention are met by providing a dental instrument mat, including a base portion having two opposite sides, a pair of racks formed longitudinally along the two opposite sides of the base portion, each rack having a plurality of spaced apart teeth, the teeth of each rack being laterally aligned with the teeth of the other rack to define a plurality of laterally disposed holding slots, each being capable of holding a dental instrument, and removable retaining means detachably coupled to the base portion, for maintaining dental instruments in the holding slots during autoclaving.

These and other features and advantages of the dental instrument mat of the present invention will become more apparent with reference to the following detailed description and drawings.

DETAILED DESCRIPTION OF THE PREFERRED EMBODIMENTS

Figure 1:
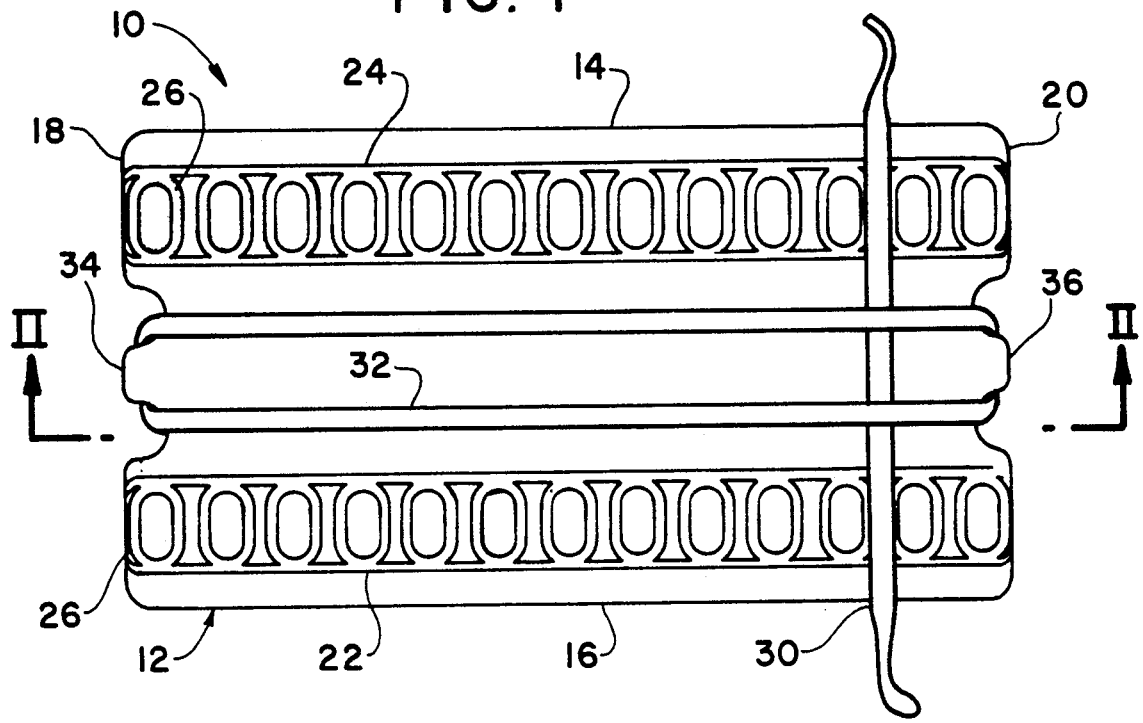
FIG. 1 is a top plan view of a first, preferred embodiment of a dental instrument mat according to the present invention.
Figure 2:
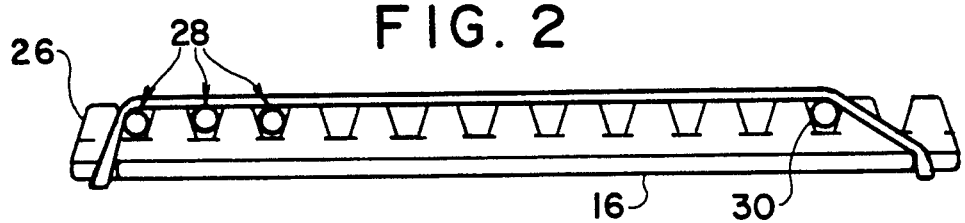
FIG. 2 is a side elevational view, partly in section of the dental instrument mat of FIG. 1, taken along line II-II.
Figure 3:
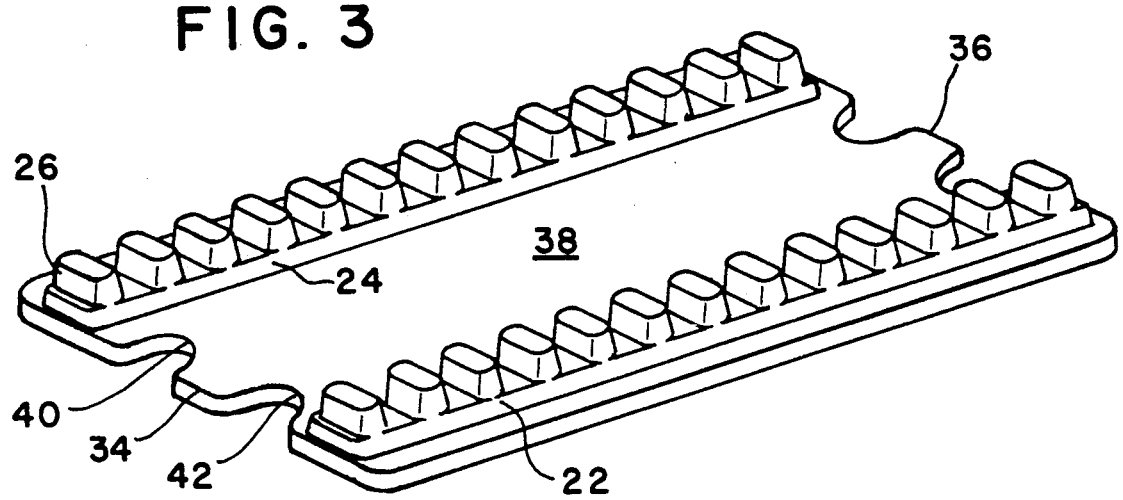
FIG. 3 is a perspective view of the embodiment of FIG. 1 with the retaining means and dental instruments removed therefrom.
Figure 4:
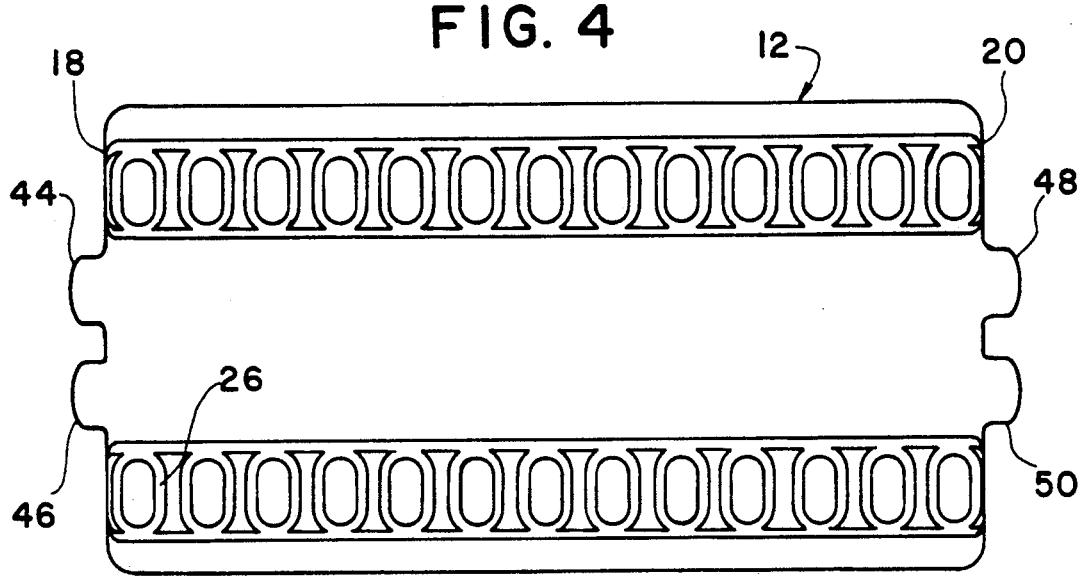
FIG. 4 is a top plan view of a second, preferred embodiment of a dental instrument mat according to the present invention.
Figure 5:
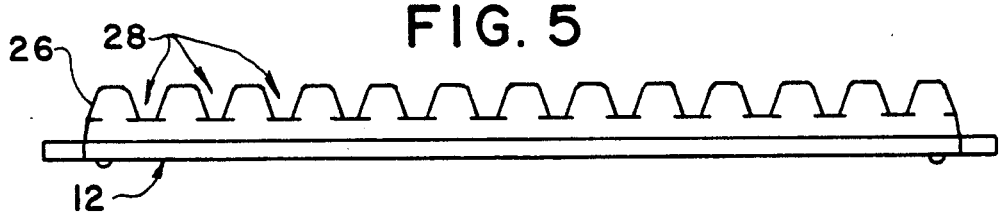
FIG. 5 is a side elevational view, partly in section, of the embodiment of FIG. 4.

Referring now to FIGS. 1 through 3, a dental instrument mat is generally referred to by the numeral 10. The mat is integrally molded of heat resistant plastic material, and includes a base portion 12 having two opposite sides 14 and 16 and two opposite ends 18 and 20.

A pair of racks 22 and 24 are formed on an upper surface of the base portion longitudinally along the two opposite sides 14 and 16. Each rack has a plurality of teeth 26 which are equidistantly spaced apart. The teeth 26 of each rack are laterally aligned with the teeth of the other rack to define a plurality of laterally disposed holding slots 28. The holding slots 28 are each capable of holding a dental instrument 30 in a transverse disposition relative to a longitudinal axis of the dental instrument mat 10.

After the instruments have been cleaned (usually the number if instruments is equal to the number of holding slots 28), the instruments are placed in their respective holding slots 28 as if being readied for the next use. Then, a removable retaining means, which is detachably coupled to the base portion 12 is placed in a holding position for maintaining the dental instruments in the holding slots 28 during autoclaving. Preferably, the removable retaining means is an elastic band which loops around two protrusions 34 and 36 which are formed at the opposite ends 18 and 20 of the base portion 12. The elastic band 32 normally has a length which is selected so that when it is looped over the protrusions 34 and 36, it is placed in tension so as to pull downwardly on the instruments and thus hold them in their holding slots 28.

After autoclaving, the elastic band, such as a rubber band, can be removed and either discarded or used again for the next sterilizing procedure. This has several advantages over the procedures used in the past, wherein the instruments were placed in the space 38 formed between the two racks 22 and 24.

In the embodiment of FIGS. 1 through 3, the protrusions 34 and 36 are each formed by two cut-out undulations 40 and 42.

In an alternative embodiment, a pair of protrusions 44, 46, and 48, 50 are formed in the opposite ends 18 and 20 of the base portion 12. In this embodiment, pairs of protrusions, comprising protrusions 44, 48 and 46, 50 may be used to apply two separate elastic bands (not shown). Alternatively, a single elastic band may be looped over the outermost sides of the protrusions so as to, in essence, provide means for applying varying tension to a single elastic band. For example, an elastic band may be looped around the protrusions 44 and 48 so as to provide a certain degree of elastic tension. However, if the elastic band having the same length is instead looped around all four protrusions, greater tension is created.

Figure 6:
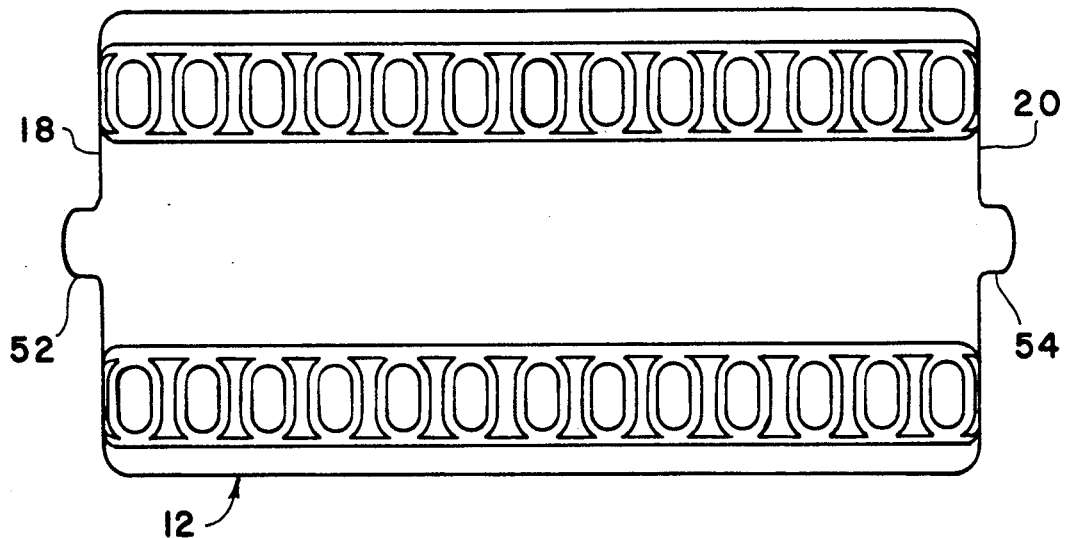
FIG. 6 is a top plan view of a dental instrument mat according to a third, preferred embodiment of the present invention.
Figure 7:
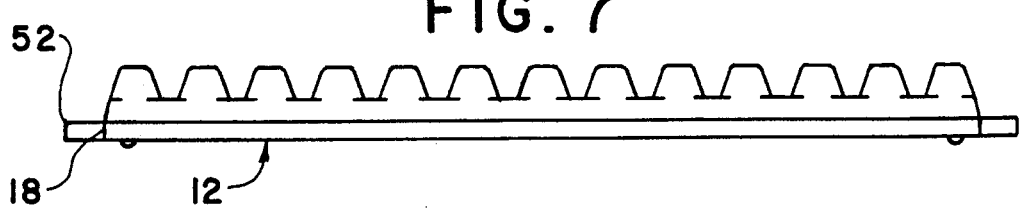
FIG. 7 is a side elevational view, partly in section, of the embodiment of FIG. 6.

In still another embodiment, illustrated in FIGS. 6 and 7, protrusions 52 and 54 extend outwardly beyond the opposite ends 18 and 20 of the base portion 12. Thus, the embodiment of FIG. 6 is similar to the embodiment of FIGS. 1 through 3, except that the protrusions extend beyond the ends of the base portion, instead of terminating in the same plane as the ends of the base portions.

Numerous modifications and adaptations of the present invention will be apparent to those so skilled in the art and thus, it is intended by the following claims to cover all such modifications and adaptations which fall within the true spirit and scope of the invention.

What is claimed is:

1. A dental instrument mat comprising:
   a base portion having two opposite sides and two opposite ends;
   a pair of racks formed longitudinally along the two opposite sides, each rack having a plurality of spaced apart teeth, the teeth of each rack being laterally aligned with the teeth of the other rack to define a plurality of laterally disposed holding slots, each being capable of holding a dental instrument, said holding slots being substantially free of frictional constraining means for holding said dental instruments; and
   removable retaining means, detachably coupled to the base portion, for tautly engaging an upwardly disposed surface of each dental instrument and downwardly biasing the same, to thereby positionally maintain dental instruments in the holding slots which are substantially free of frictional constraining means.

2. A dental instrument mat according to claim 1, wherein the removable retaining means comprises elastic retaining means.

3. A dental instrument mat according to claim 1 further comprising at least one protrusion formed at each of the opposite ends of the base portion for mounting the removable retaining means.

4. A dental instrument mat according to claim 3 wherein the removable retaining means is an elastic band which loops around the at least one protrusion formed at each of the opposite ends of the base portion.

5. A dental instrument mat according to claim 4 wherein the at least one protrusion formed at each of the opposite ends of the base portion comprises a single protrusion formed by a pair of cut out undulations.

6. A dental instrument mat according to claim 4, wherein the at least one protrusion comprises a pair of protrusions formed at each of the opposite ends of the base portion, each pair of protrusions extending longitudinally beyond the opposite ends of the base portion.

7. A dental instrument mat according to claim 4, wherein the at least one protrusion comprises a single protrusion formed at each of the opposite ends of the base portion, each protrusion extending longitudinally beyond the opposite ends of the base portion.

8. A dental instrument mat comprising:
   a base portion having two opposite sides and two opposite ends;
   a pair of racks formed longitudinally along the two opposite sides, each rack having a plurality of spaced apart teeth, the teeth of each rack being laterally aligned with the teeth of the other rack to define a plurality of laterally disposed holding slots, each holding slot being capable of holding a dental instrument, said holding slots being substantially free of frictional constraining means for holding said dental instruments;
   at least one protrusion formed at each of the opposite ends of the base portion; and
   an elastic band detachably coupled to the base portion by looping over the at least one protrusion provided at each of the opposite ends of the base portion, thereby placing the elastic band in tension for tautly engaging an upwardly disposed surface of each dental instrument and downwardly biasing the same, to thereby positionally maintain dental instruments in the holding slots which are substantially free of frictional constraining means.

9. A dental instrument mat according to claim 8, wherein the at least one protrusion formed at each of the opposite ends of the base portion is below the dental instruments when held in holding slots so that as the elastic band is placed in tension, the dental instruments are elastically biased downwardly into the holding slots.

* * * * *